(12) United States Patent
Mitchell et al.

(10) Patent No.: US 10,401,319 B2
(45) Date of Patent: Sep. 3, 2019

(54) STRUCTURAL HEALTH MONITORING SYSTEM

(71) Applicant: The Boeing Company, Chicago, IL (US)

(72) Inventors: Timothy M. Mitchell, Seattle, WA (US); John Michael Hood, Lake Stevens, WA (US); Devon Alexander Baughen, Sarasota, FL (US)

(73) Assignee: The Boeing Company, Chicago, IL (US)

( * ) Notice: Subject to any disclaimer, the term of this patent is extended or adjusted under 35 U.S.C. 154(b) by 277 days.

(21) Appl. No.: 15/407,226

(22) Filed: Jan. 16, 2017

(65) Prior Publication Data

US 2018/0202959 A1 Jul. 19, 2018

(51) Int. Cl.
| | |
|---|---|
| *G01N 27/20* | (2006.01) |
| *G01N 27/04* | (2006.01) |
| *G01N 17/04* | (2006.01) |
| *G01M 5/00* | (2006.01) |

(52) U.S. Cl.
CPC .......... *G01N 27/20* (2013.01); *G01M 5/0016* (2013.01); *G01M 5/0083* (2013.01); *G01N 17/04* (2013.01); *G01N 27/041* (2013.01)

(58) Field of Classification Search
CPC ...... G01N 27/20; G01N 27/041; G01N 17/04; G01M 5/0083; G01M 5/0016
USPC .................................. 324/693, 691, 649, 600
See application file for complete search history.

(56) References Cited

U.S. PATENT DOCUMENTS

| | | | |
|---|---|---|---|
| 6,617,972 B2* | 9/2003 | Takarada | G08B 21/0484 324/538 |
| 7,621,193 B2 | 11/2009 | Fay et al. | |
| 8,040,243 B2 | 10/2011 | Bommer et al. | |
| 8,054,092 B2 | 11/2011 | Fay et al. | |
| 8,138,773 B2 | 3/2012 | Fay et al. | |
| 8,237,548 B2 | 8/2012 | Fay et al. | |
| 8,779,729 B2* | 7/2014 | Shiraishi | G06F 1/3212 320/155 |
| 2007/0114422 A1 | 5/2007 | Berkcan et al. | |

(Continued)

OTHER PUBLICATIONS

European Patent Office, Extended European Search Report regarding European Patent Application No. 17198042.8-1001, dated Apr. 26, 2018, 8 pages.

(Continued)

*Primary Examiner* — Giovanni Astacio-Oquendo
(74) *Attorney, Agent, or Firm* — Kolisch Hartwell, P.C.

(57) ABSTRACT

A structural health monitoring system may include a structural health monitoring device comprising a measuring circuit attachable to a target area of a workpiece. The measuring circuit may be communication with a radio circuit having an antenna configured to facilitate offboard communication. The measuring circuit may be configured to measure an impedance of the target area of the workpiece, and the processing circuit may be configured to determine a change in the impedance of the target area indicative of a change in structural health of the workpiece. An ambient energy harvester circuit may be configured to provide electrical power to the measuring circuit. A remote reader may wirelessly interrogate the structural health monitoring device to obtain information regarding the change in the impedance of the target area.

20 Claims, 6 Drawing Sheets

(56) References Cited

U.S. PATENT DOCUMENTS

| | | | | |
|---|---|---|---|---|
| 2012/0098518 A1* | 4/2012 | Unagami | ............ | G01R 22/066 |
| | | | | 324/74 |
| 2016/0178714 A1* | 6/2016 | Fautz | .................. | G01R 33/483 |
| | | | | 324/309 |
| 2017/0319097 A1* | 11/2017 | Amthor | .................. | A61B 5/055 |
| 2018/0024214 A1* | 1/2018 | Bhat | .................. | G01R 33/4828 |
| | | | | 324/309 |

OTHER PUBLICATIONS

European Patent Office, Examination Report regarding European Patent Application No. 17198042.8-1001, dated May 21, 2019, 4 pages.

\* cited by examiner

STRUCTURAL HEALTH MONITORING SYSTEM

FIELD

This disclosure relates to systems and methods for structural health management and, more particularly, to devices, systems and methods for monitoring a workpiece and for providing information regarding the structural health of the workpiece.

INTRODUCTION

A variety of structures are routinely inspected to determine the health of the structure and to identify any issues that may require further inspection, maintenance or repair. For example, buildings, bridges and the like may be regularly inspected to identify the onset of any issues that may potentially weaken or otherwise eventually render the structure unsuitable for its intended use. Similarly, vehicles (e.g., airplanes, trains, ships) may be regularly inspected in order to similarly identify any issues that merit further action.

Commercial aircraft, for example, may be subject to periodic scheduled inspections. During these inspections, the aircraft must generally be removed from service to permit an intensive visual inspection of the aircraft to be conducted. In this regard, at least some aircraft inspections involve substantial disassembly of the aircraft in order to visually inspect the various components. For example, disassembly of an aircraft may be required in order to inspect for corrosion or fatigue damage and/or to identify crack propagation in regions of the aircraft that have limited accessibility.

By way of further example, to visually inspect hard-to-access but susceptible portions of an aircraft, such as the floor support structure or the fin-to-body or wing-to-body connections, significant disassembly and adjacent equipment removal may be necessary. The time and effort required to visually inspect these portions of the aircraft may be substantial, thereby potentially requiring the aircraft to remain out of service for a substantial period of time. Additionally, the removal or disassembly of certain components may result in difficulty resealing or reattaching those components with the same degree of integrity as during original manufacture of the aircraft. Furthermore, the disassembly itself may accidentally damage the structure and/or the removed component such that additional maintenance or repair activities are required.

In addition to the time and effort required to conduct a visual inspection, reliance upon scheduled inspections may be disadvantageous in that scheduled inspections may require the aircraft to be temporarily taken out of service unnecessarily, e.g., in instances where the aircraft has no structural issues and is determined not to be in need of any repair. Conversely, a scheduled inspection may occur later than desired in other instances in which a structural issue has developed. In these examples, the time that occurs between scheduled inspections is such that the structural issue may be allowed to propagate or otherwise damage the surrounding structure. More extensive repairs may be required than if the structural issue had been identified sooner.

It would therefore be desirable to provide improved techniques for monitoring and inspecting a structure in an efficient, cost effective, and timely manner. In this regard, it would be desirable to provide improved inspection techniques for identifying structural fatigue, cracks, corrosion, or other structural issues in a timely fashion following their inception, while not requiring the structure to be removed from service for a prolonged period. Additionally, it would be desirable to provide an improved technique for monitoring and inspecting structures which reduces the disassembly otherwise required for conventional visual inspection.

SUMMARY

Structural health monitoring systems and methods according to the present teachings overcome the problems above by remaining attached to selected target regions of the structure, monitoring the structural health of the target regions by periodically measuring electrical impedance and wirelessly communicating that information to a remote reader device, such as the onboard network system of a host aircraft. These monitoring systems may include ambient energy harvesting circuits configured to power the electrical measurement and/or information transmission.

In some embodiments, a structural health monitoring device may include: a measuring circuit including a processing circuit communicatively coupled to a pair of electrodes attachable to a target area of a workpiece, the measuring circuit in communication with a radio circuit having an antenna configured to facilitate offboard communication; and an energy harvester circuit configured to provide electrical power to the measuring circuit; wherein the measuring circuit is configured to measure an impedance of the target area of the workpiece; and wherein the processing circuit is configured to determine a change in the impedance of the target area indicative of a change in structural health of the workpiece.

In some embodiments, a structural health monitoring system may include: a structural health monitoring device comprising a measuring circuit including a processing circuit communicatively coupled to a pair of electrodes attachable to a target area of a workpiece, the measuring circuit in communication with a radio circuit having an antenna configured to facilitate offboard communication; and an energy harvester circuit configured to provide electrical power to the measuring circuit; wherein the measuring circuit is configured to measure an impedance of the target area of the workpiece; and wherein the processing circuit is configured to determine a change in the impedance of the target area indicative of a change in structural health of the workpiece; and a reader configured to wirelessly interrogate the structural health monitoring device to obtain information regarding the change in the impedance of the target area.

In some embodiments, a method for structural health monitoring may include: monitoring structural health of a workpiece using a structural health monitoring device coupled to the workpiece, the structural health monitoring device comprising a measuring circuit including a processing circuit communicatively coupled to a pair of electrodes attached to a target area of the workpiece, wherein the measuring circuit is configured to measure an impedance of the target area of the workpiece, and wherein the processing circuit is configured to determine a change in the measured impedance of the target area indicative of a change in structural health of the workpiece; harvesting environmental energy using an energy harvesting circuit of the structural health monitoring device to provide electrical power to the structural health monitoring device; and transmitting information regarding the measured impedance of the target area to an offboard reader using a radio circuit of the structural health monitoring device in communication with the measuring circuit.

Features, functions, and advantages may be achieved independently in various embodiments of the present disclosure, or may be combined in yet other embodiments, further details of which can be seen with reference to the following description and drawings.

DESCRIPTION

Various aspects and examples of a remote structural health monitoring system, as well as related methods, are described below and illustrated in the associated drawings. Unless otherwise specified, a structural health monitoring system and/or its various components may, but are not required to, contain at least one of the structure, components, functionality, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Definitions

The following definitions apply herein, unless otherwise indicated.

"Substantially" means to be essentially conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

Overview

In general, a structural health monitoring system according to the present teachings may include a structural health monitoring device coupled to a target area of a workpiece, and a reader configured to wirelessly interrogate the structural health monitoring device to obtain information regarding a change in the electrical characteristic(s) of the target area. The structural health monitoring device may include a measuring circuit, which includes a processing circuit communicatively coupled to a pair of electrodes that attach to the target area of the workpiece. The measuring circuit is also in communication with a radio circuit having an antenna configured to facilitate offboard communication. The structural health monitoring device may also include an energy harvester circuit configured to provide electrical power to the measuring circuit, e.g., by harvesting thermal, solar, or other ambient energy. In some examples, the measuring circuit is configured to measure an electrical impedance (e.g., resistance) of the target area of the workpiece. The processing circuit of the device is configured to determine a change in the electrical characteristic(s), (e.g., impedance) of the target area indicative of a change in structural health of the workpiece. For example, fatigue-induced stress or corrosion of the target area may be indicated by a change in its electrical impedance.

Aspects of the remote structural health monitoring system described herein may be embodied as a computer method, computer system, or computer program product. Accordingly, aspects of the structural health monitoring system may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the structural health monitoring system may take the form of a computer program product embodied in a computer-readable medium (or media) having computer-readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the structural health monitoring system may be written in one or any combination of programming languages, including an object-oriented programming language such as Java, Smalltalk, C++, and/or the like, and conventional procedural programming languages, such as C. Mobile apps may be developed using any suitable language, including those previously mentioned, as well as Objective-C, Swift, C#, HTML5, and the like. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the structural health monitoring system are described below with reference to flowchart illustrations and/or block diagrams of methods, apparatuses, systems, and/or computer program products. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks.

Any flowchart and/or block diagram in the drawings is intended to illustrate the architecture, functionality, and/or operation of possible implementations of systems, methods, and computer program products according to aspects of the structural health monitoring system. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

Examples, Components, and Alternatives

The following sections describe selected aspects of exemplary structural health monitoring systems as well as related systems, devices, and/or methods. The examples in these sections are intended for illustration and should not be interpreted as limiting the entire scope of the present disclosure. Each section may include one or more distinct embodiments or examples, and/or contextual or related information, function, and/or structure.

Illustrative Structural Health Monitoring System

Figure 1:
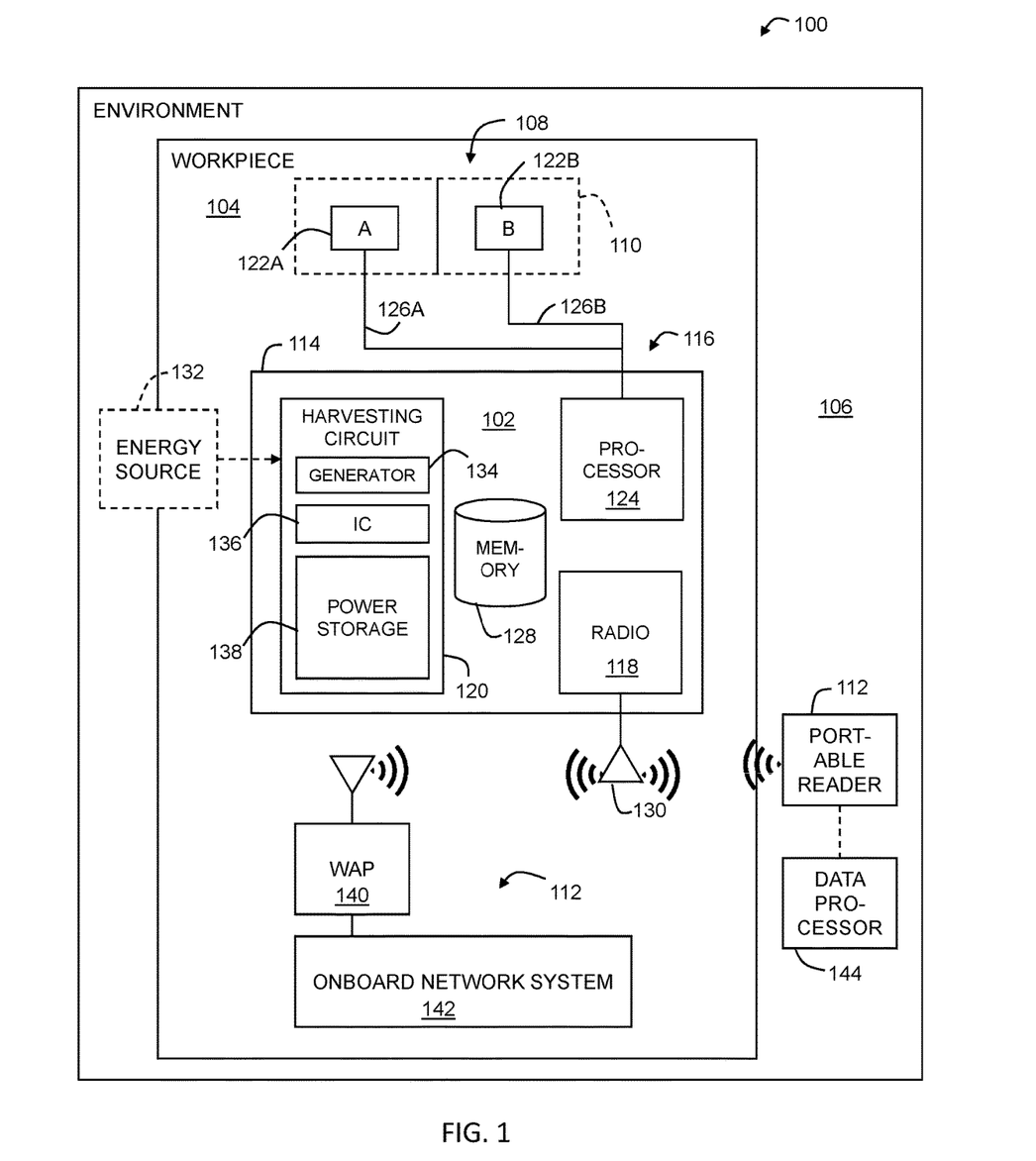
FIG. 1 is a schematic diagram of an illustrative structural health monitoring system in accordance with aspects of the present disclosure.

As shown in FIG. 1, this section describes an illustrative structural health monitoring system 100. System 100 is an example of the structural health monitoring system described in the Overview above.

System 100 includes one or more structural health monitoring device(s) 102 coupled to a workpiece 104 disposed in an environment 106. Workpiece 104 may include any suitable host structure for which structural health monitoring is desired. For example, workpiece 104 may include an aircraft, a vehicle, a bridge, a ship, a spacecraft, or the like, or any portion or component thereof. Workpiece 104 operates, interacts with, and/or otherwise exists in environment 106, which may include a natural or artificial environment, and may include ambient features such as sunlight, wind, atmospheric pressure, moisture, water, noise, vibration, thermal gradients, and/or the like, or any combination of these.

With continuing reference to FIG. 1, each structural health monitoring device 102 may include any suitable circuit and interface configured to determine an electrical characteristic 108 of a respective target monitoring region 110 of workpiece 104 and wirelessly transmit information regarding that characteristic, on demand, to a remote reader device 112. Device 102 in the example depicted in FIG. 1 includes a body 114, which may include a printed circuit board and/or a housing or case for the device, a measuring circuit 116, a radio circuit 118, and an energy harvesting circuit 120 configured to provide electrical power to the measuring circuit and the radio circuit.

Measuring circuit 116 may include any suitable circuit and/or module configured to measure one or more electrical characteristics of target monitoring region 110. In this example, measuring circuit 116 includes a pair of electrodes 122A and 122B coupled to a processing circuit 124 by respective conductive wires or leads 126A and 126B. Electrodes 122A and 122B may each be referred to as a sensor or half-sensor.

Processing circuit 124 may include any suitable circuit and/or module configured to receive sensor input from electrodes 122A and 122B, and to determine an electrical measurement of target monitoring region 110 from the electrodes. In some examples, processing circuit 124 may perform signal conditioning. In some examples, processing circuit 124 may include a microprocessor. In some examples, processing circuit 124 may be configured to carry out one or more steps of selected methods or algorithms (e.g., method 200 described below). Processing circuit 124 is in communication with, and may include, a memory store 128. Memory store 128 may include instructions (e.g., executable by the microprocessor) for carrying out functions of the processing circuit. In some examples, data corresponding to measurements of the electrical characteristics of target monitoring region 110 may be stored in memory store 128, e.g., for later retrieval, for trend analysis, for transmission offboard the device, for comparison to expected values or ranges, and/or the like.

Radio circuit 118 is in communication with processing circuit 124, e.g., for receiving measurement data, and may include any circuit and/or module configured to transmit and receive modulated electromagnetic signals wirelessly via an antenna 130. Radio circuit 118 is configured to communicate with remote reader device 112. For example, radio circuit 118 and reader 112 may both operate under a standard protocol, such as IPv6 over Low power Wireless Personal Area Networks (i.e., 6LoWPAN). In some examples, radio circuit 118 may comprise a ZigBee device. In some examples, radio circuit 118 may comprise a Bluetooth LE (i.e., Bluetooth Smart) device. In some examples, radio circuit 118 may be configured as a radio-frequency identification (RFID) system, such that reader 112 comprises an RFID reader.

Energy harvesting circuit 120 is configured to provide electrical power to measuring circuit 116 and/or radio circuit 118. Energy harvesting circuit 120 may include any suitable circuit and/or module configured to collect ambient energy from an energy source 132 of environment 106 and/or workpiece 104, and to convert that energy into electricity for use or storage. In this example, energy harvesting circuit 120 includes a generator device 134 coupled to an energy harvesting integrated circuit (IC) 136, and an energy storage device 138. Generator device 134 may include any suitable device configured to collect ambient energy (e.g., thermal gradient energy, vibration, light, sound, etc.) from source 132 and convert it to electrical power, such as a thermoelectric generator (TEG) or a piezoelectric or photovoltaic (PV) cell. In some examples antenna 130 may supplement or function as generator device 134, such as when radio circuit 118 is configured in the manner of an RFID system.

Energy harvesting IC 136 may include any suitable device configured to efficiently acquire and manage the small amounts of power (in the μW to mW range) generated by generator device 134. For example, energy harvesting IC's (also referred to as ultra low-power boost converters) available from Texas Instruments, currently sold under the designation of BQ25504, BQ25505, and BQ25570 may be suitable for use in circuit 120.

Energy collected by circuit 120 is provided directly to the other circuits of device 102 and/or is stored in energy storage device 138. Energy storage device 138 may include a rechargeable lithium ion (Li-ion) battery, an ultracapacitor, a lead acid battery, a nickel cadmium battery (NiCad), and/or the like, or any combination of these. In some examples, alternating-current (AC) power may be provided to the measuring circuit, for example, by circuit 120 via a power inverter. This may facilitate electrical measurements relating to AC power, such as frequency response or inductance.

The one or more structural health monitoring devices 102 may be referred to as a detector or a detector device. Reader device 112 is a separate device from detector 102, and may include any suitable wireless communication device configured to communicate with detector 102 for the purposes of interrogation and/or transmission of measurement information from detector 102 regarding target monitoring region 110. In some examples, reader device 112 is a portable reader, such as a handheld electronic device carried by a technician for the purpose of interrogating one or more detectors 102 located in various regions on workpiece 104. In some examples, workpiece 104 comprises a portion of an aircraft, and reader device 112 includes a wireless access point (WAP) 140 of an onboard network system (ONS) 142 of the aircraft. In either case, reader device 112 may be placed in communication with a data processor 144 for the further aggregation, analysis, and reporting of the measurement data from one or more detector devices 102 on one or more workpieces 104.

Illustrative Structural Health Monitoring Method

This section describes steps of an illustrative method for monitoring the structural health of a workpiece. Aspects of structural health monitoring systems and devices described above may be utilized in the method steps described below. Where appropriate, reference may be made to components and systems that may be used in carrying out each step. These references are for illustration, and are not intended to limit the possible ways of carrying out any particular step of the method.

In general, steps of an illustrative method for structural health monitoring may include monitoring structural health of a workpiece (e.g., workpiece 104) using a structural health monitoring device (e.g., device 102) coupled to the workpiece, the structural health monitoring device comprising a measuring circuit (e.g., measuring circuit 116) including a processing circuit (e.g., processing circuit 124) communicatively coupled to a pair of electrodes (e.g., electrodes 122A, 122B) attached to a target area (e.g., target monitoring region 110) of the workpiece. The measuring circuit is configured to measure an impedance of the target area of the workpiece. The processing circuit is configured to determine a change in the measured impedance of the target area indicative of a change in structural health of the workpiece. The method may further include harvesting environmental energy (e.g., energy source 132) using an energy harvesting circuit (e.g., energy harvesting circuit 120) of the structural health monitoring device to provide electrical power to the structural health monitoring device. Information regarding the measured impedance of the target area may be transmitted to an offboard reader (e.g., reader device 112) using a radio circuit (e.g., radio circuit 118) of the structural health monitoring device in communication with the measuring circuit.

In some examples, the measured impedance of the target area of the workpiece may be compared to an expected impedance range. In response to the measured impedance being outside the expected impedance range, an alert signal may be sent to the offboard reader (e.g., by radio circuit 118).

In some examples, the measured impedance may be stored in a memory store (e.g., memory store 128) of the measuring circuit. In some examples, harvesting environmental energy includes harvesting thermal energy using a thermoelectric generator (TEG) and/or a photovoltaic (PV) cell coupled to an energy harvester integrated circuit (IC).

In some examples, the workpiece comprises a portion of an aircraft, and the offboard reader comprises an onboard network system (ONS) of the aircraft.

Figure 2:
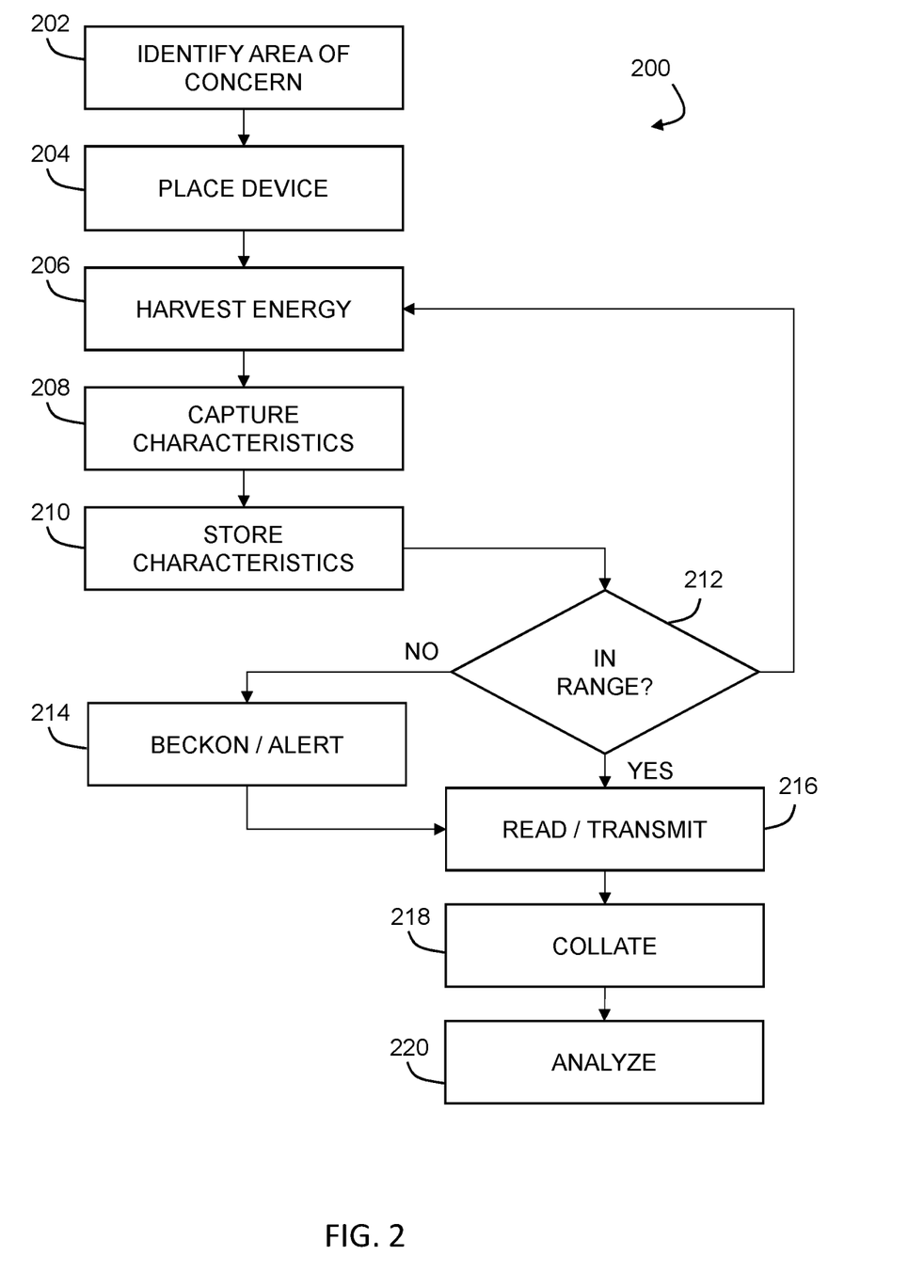
FIG. 2 is a flow chart depicting steps of an illustrative method for monitoring structural health of a workpiece, according to the present teachings.

Turning to FIG. 2, a flowchart is depicted, illustrating steps performed in another illustrative method for monitoring the structural health of a workpiece. The flowchart of FIG. 2 may not recite the complete process or all steps of the method. FIG. 2 depicts multiple steps of a method, generally indicated at 200, which may be performed in conjunction with structural health monitoring system 100 and device 102, as well as one or more steps of the general method described above. Although various steps of method 200 are described below and depicted in FIG. 2, the steps need not necessarily all be performed, and in some cases may be performed in a different order than the order shown.

At step 202, an area of concern on a workpiece may be identified. For example, certain areas or regions of an aircraft are often more susceptible to corrosion or fatigue failure. These areas of concern correspond to the target monitoring regions described with respect to FIG. 1. Identifying the area of concern may be done based on previous experience, known areas of higher risk for the type of workpiece (e.g., aircraft model), age of the workpiece, etc., or a combination of these.

At step 204, a structural health monitoring device (e.g., device 102) is placed at the area of concern. For example, the device may be coupled to the workpiece, with its electrodes or sensors attached to the target monitoring region. The device may be mounted, removably or otherwise, to the workpiece, such as by bolting or adhering. In some examples, this may involve placing one electrode on either side of an area being monitored, such that the electrical characteristic is measured across the area of concern. In general, the device is durably coupled to the workpiece in such a way that the device remains securely attached during operational use of the workpiece. In other words, in this example, the device is intended to be a long-term or semi-permanent monitoring device, rather than a portable device used for one-time or ad hoc measurements.

At step 206, ambient energy from the environment and/or the workpiece may be harvested and converted to electrical power for use by the device. As a long-term monitoring device, often placed in hard-to-access locations, powering the structural health monitoring device may present a challenge using conventional methods such as direct power or replaceable batteries. Accordingly, energy may be harvested from the environment, such as piezoelectric energy from vibration, photovoltaic energy from light or sunlight, thermoelectric energy from temperature fluctuation and/or gradients, fluidic energy from local air movement and/or water movement, and/or the like, or any combination of these. An onboard power storage device, such as a lithium-ion battery, may be used to store the harvested energy.

At step 208, one or more electrical characteristics of the area of concern are captured (i.e., measured) by the monitoring device. For example, a resistance or impedance may be measured between the two electrodes of the device, e.g., using ohmmeter techniques familiar to one having skill in the art.

At step 210, the characteristic(s) measured in step 208 are stored onboard the monitoring device. For example, information regarding the measured characteristics may be stored in an onboard memory store (e.g., persistent storage).

At step 212, the measured characteristic(s) are compared to an expected value or range of values. This expected value or range may be determined by any suitable method, such as by basing the range on historical data across similar workpieces, the age or cycle count of the workpiece, the location of the workpiece, etc.

At step 214, if the measured characteristic is outside the expected range, an alert signal is broadcast, indicating that the monitoring device should be interrogated and investigated further. In some examples, an alert signal may be sent when a series of measurements (e.g., three in a row) indicates a trend toward an out-of-specification condition.

At step 216, either in response to the alert signal of step 214, on a selected periodic basis, as needed, or on user demand, the stored information regarding the measured electrical characteristics of the area of concern is transmitted wirelessly to an interrogating reader device. As described above, the reader device may include a portable reader, or may be integrated with the workpiece, such as a wireless access point of an onboard network system (ONS) of an aircraft.

At step 218, the information relating to electrical measurements is collated and compiled by a data processing system (e.g., a computer or computer network).

At step 220, measurements from across time, across a workpiece type or model, etc., may be analyzed for trends and correlated with related data (e.g., temperature, known events). This analysis may further be used in one or more predictive models. In some examples, corrosion and/or fatigue-related measurements from structural health monitoring devices associated with a plurality of workpieces (e.g., a fleet of aircraft) may be analyzed. For example, analysis may be performed for commonalities and trends relating to aircraft model, type, age, and/or thermal cycles. In some examples, analysis may relate to a selected target monitoring region or area of concern common to multiple workpieces (e.g., wing-to-body connection areas for aircraft).

Illustrative Aircraft and Associated Method

Figure 3:
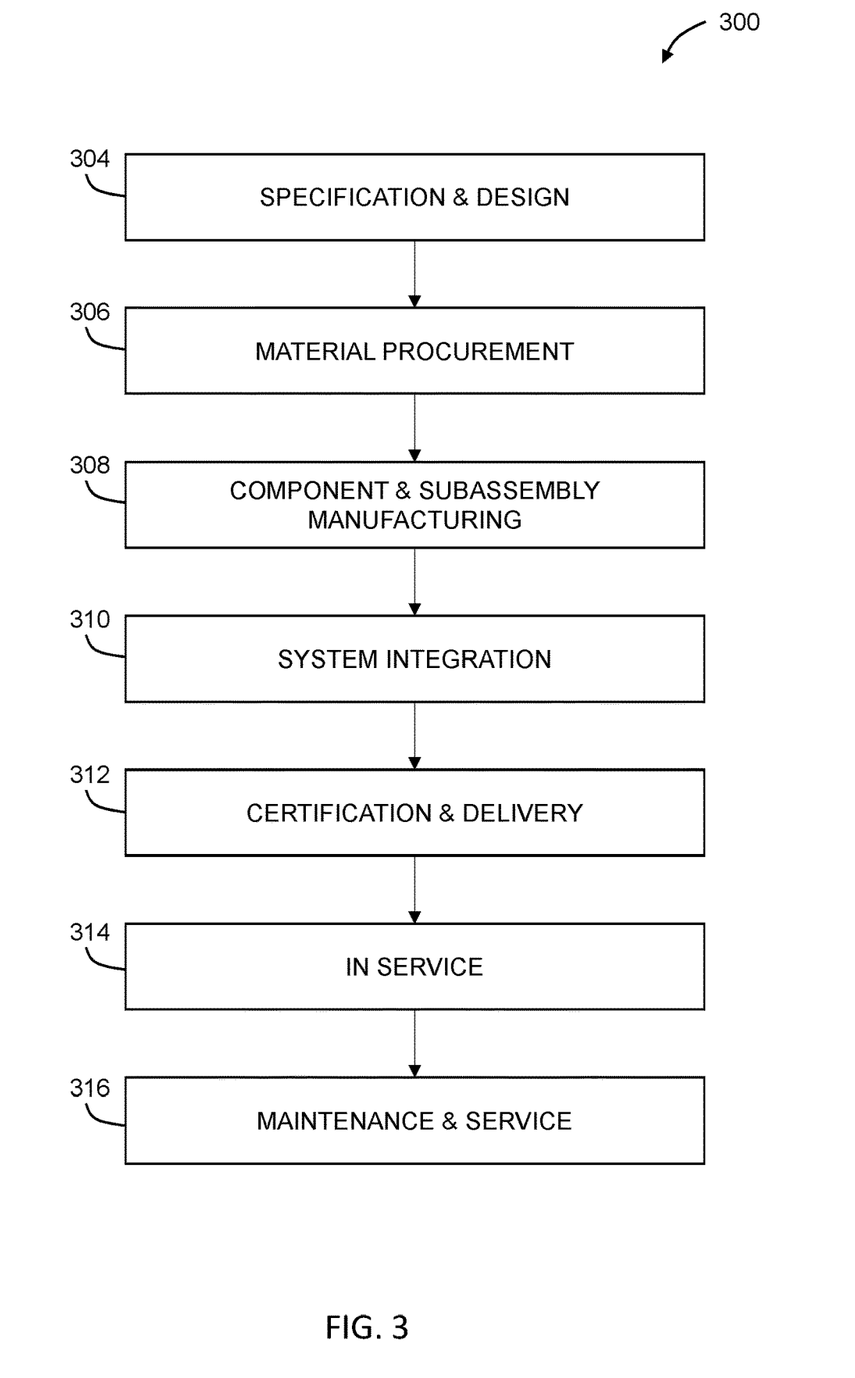
FIG. 3 is a flow chart depicting steps of illustrative aircraft manufacturing and service method.
Figure 4:
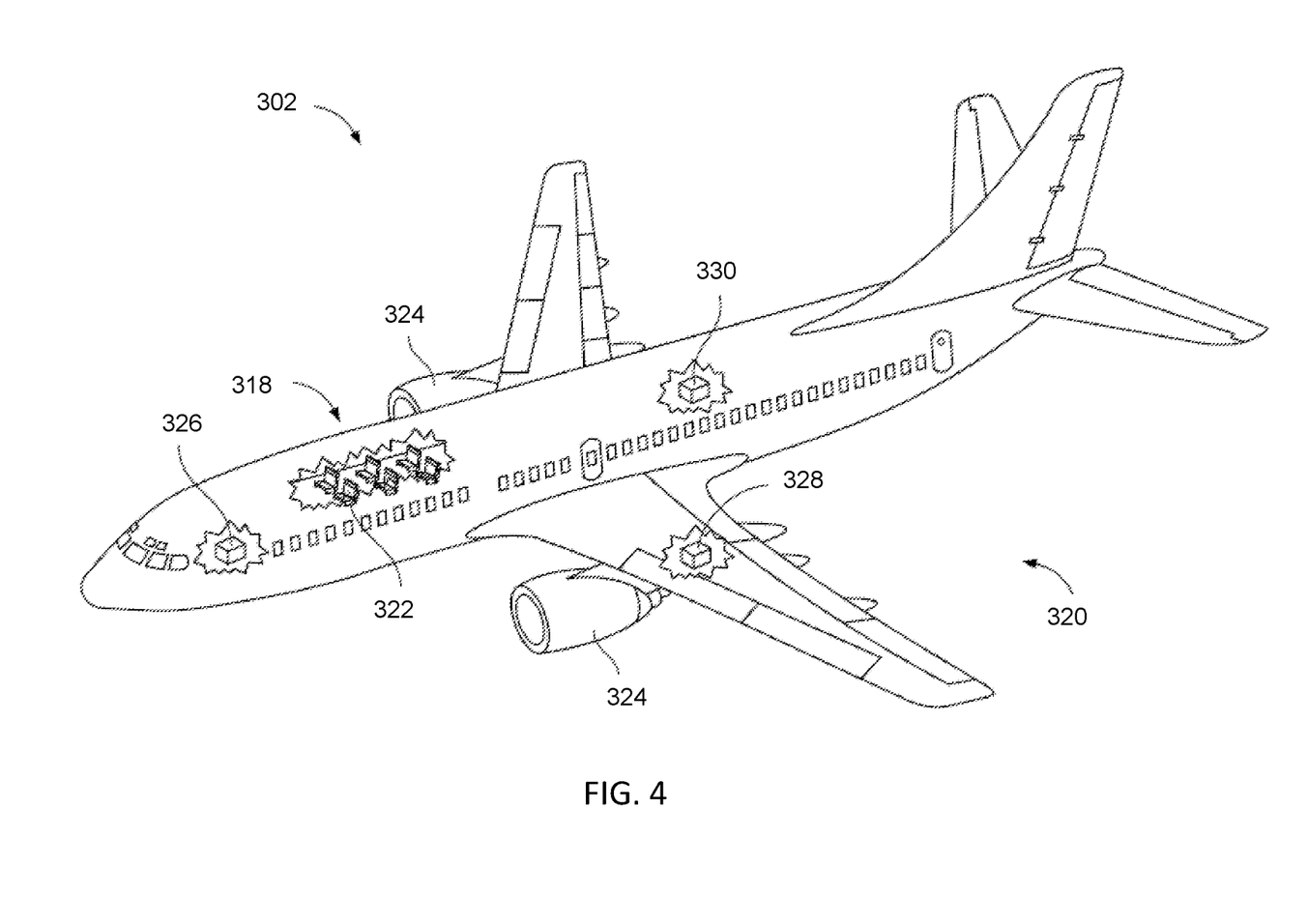
FIG. 4 is an isometric view of an illustrative aircraft.

Examples of the present disclosure may be described in the context of an illustrative aircraft manufacturing and service method 300 as shown in FIG. 3 and an illustrative aircraft 302 as shown in FIG. 4. For example, aircraft 302 may comprise a workpiece, as described above. One or more structural health monitoring devices may be installed in target monitoring regions of the aircraft, e.g., during system integration. In some examples, communication with the monitoring devices may be carried out using an onboard network system of the aircraft.

During pre-production, method 300 may include specification and design (block 304) of aircraft 302 and material procurement (block 306). During production, component and subassembly manufacturing (block 308) and system integration (block 310) of aircraft 302 may take place. Thereafter, aircraft 302 may go through certification and delivery (block 312) to be placed in service (block 314). While in service, aircraft 302 may be scheduled for routine maintenance and service (block 316). Routine maintenance and service may include modification, reconfiguration, refurbishment, etc., of one or more systems of aircraft 302.

Each of the processes of method 300 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 4, aircraft 302 produced by illustrative method 300 may include an airframe 318 with a plurality of high-level systems 320 and an interior 322. Examples of high-level systems 320 include one or more of a propulsion system 324, an electrical system 326, a hydraulic system 328, and an environmental system 330. Any number of other systems may be included. Although an aerospace example is shown, the principles disclosed herein may be applied to other industries, such as the automotive industry. Accordingly, in addition to aircraft 302, the principles disclosed herein may apply to other vehicles, e.g., land vehicles, marine vehicles, space vehicles, etc.

Apparatuses and methods shown or described herein may be employed during any one or more of the stages of the manufacturing and service method 300. For example, components or subassemblies corresponding to component and subassembly manufacturing (block 308) may be fabricated or manufactured in a manner similar to components or subassemblies produced while aircraft 302 is in service (block 314). Also, one or more examples of the apparatuses, methods, or combinations thereof may be utilized during production stages 308 and 310, for example, by substantially expediting assembly of or reducing the cost of aircraft 302. Similarly, one or more examples of the apparatus or method realizations, or a combination thereof, may be utilized, for example and without limitation, while aircraft 302 is in service (block 314) and/or during maintenance and service (block 316).

Illustrative Data Processing System

Figure 5:
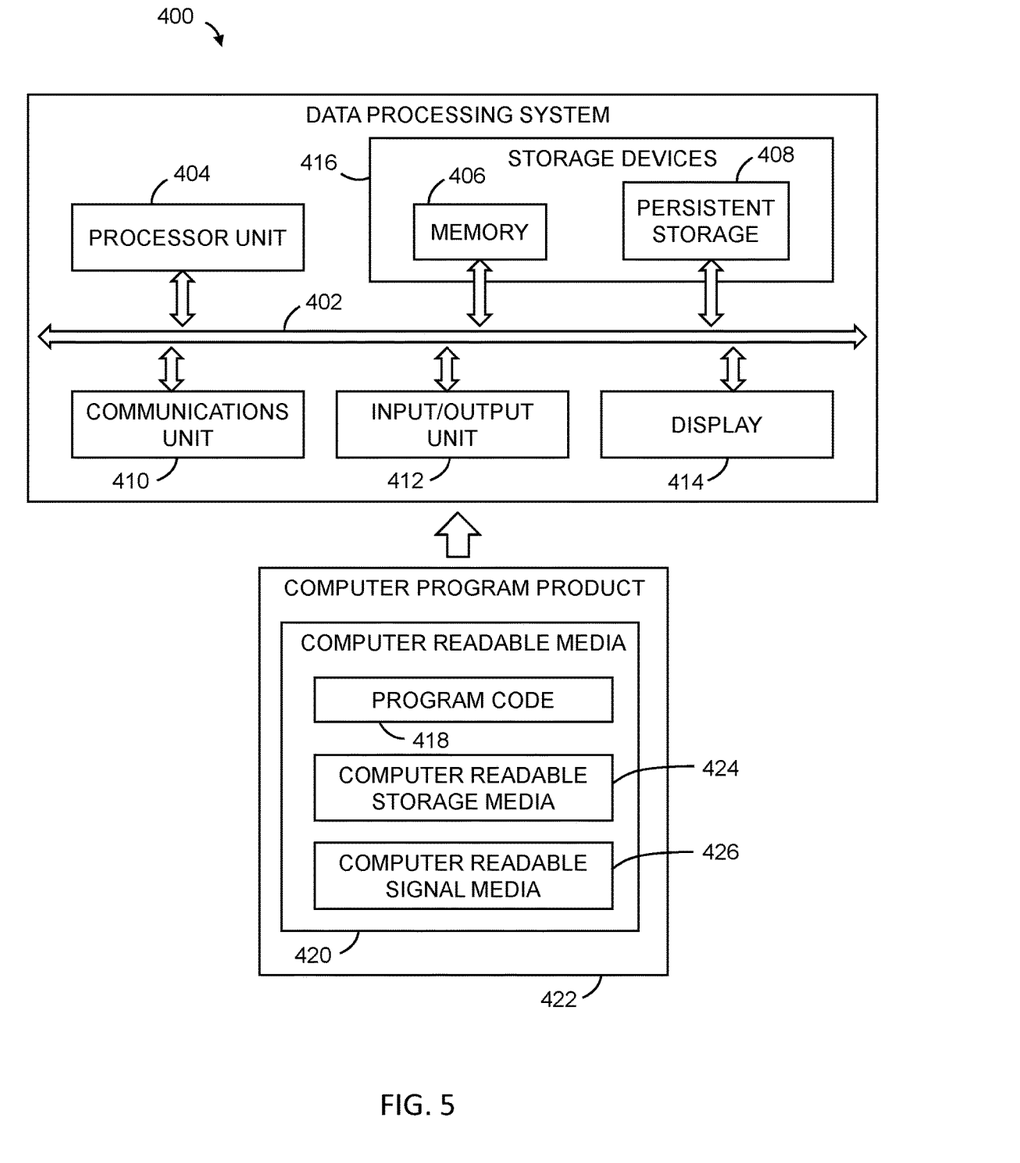
FIG. 5 is a schematic diagram of an illustrative data processing system suitable for use with and/or inclusion in one or more aspects of the present disclosure.

As shown in FIG. 5, this example describes a data processing system 400 (also referred to as a computer) in accordance with aspects of the present disclosure. In this example, data processing system 400 is an illustrative data processing system suitable for implementing aspects of a structural health monitoring system in accordance with aspects of the present disclosure. More specifically, in some examples, devices that are embodiments of data processing systems (e.g., servers, computers) may be used to collate and analyze information related to the electrical measurements taken by system 100. In some examples, aspects of data processing system 400 may be used in a processing circuit of structural health monitoring device 102 (e.g., circuit 124).

In this illustrative example, data processing system 400 includes communications framework 402. Communications framework 402 provides communications between processor unit 404, memory 406, persistent storage 408, communications unit 410, input/output (I/O) unit 412, and display 414. Memory 406, persistent storage 408, communications unit 410, input/output (I/O) unit 412, and display 414 are examples of resources accessible by processor unit 404 via communications framework 402.

Processor unit 404 serves to run instructions that may be loaded into memory 406. Processor unit 404 may be a number of processors, a multi-processor core, or some other type of processor, depending on the particular implementation. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information, such as, for example, without limitation, data, program code in functional form, and other suitable information either on a temporary basis or a permanent basis.

Storage devices 416 also may be referred to as computer-readable storage devices in these examples. Memory 406, in these examples, may be, for example, a random access memory or any other suitable volatile or non-volatile storage device. Persistent storage 408 may take various forms, depending on the particular implementation.

For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output (I/O) unit 412 allows for input and output of data with other devices that may be connected to data processing system 400. For example, input/output (I/O) unit 412 may provide a connection for user input through a keyboard, a mouse, and/or some other suitable input device. Further, input/output (I/O) unit 412 may send output to a printer. Display 414 provides a mechanism to display information to a user.

Instructions for the operating system, applications, and/or programs may be located in storage devices 416, which are in communication with processor unit 404 through communications framework 402. In these illustrative examples, the instructions are in a functional form on persistent storage 408. These instructions may be loaded into memory 406 for execution by processor unit 404. The processes of the different embodiments may be performed by processor unit 404 using computer-implemented instructions, which may be located in a memory, such as memory 406.

These instructions are referred to as program instructions, program code, computer usable program code, or computer-readable program code that may be read and executed by a processor in processor unit 404. The program code in the different embodiments may be embodied on different physical or computer-readable storage media, such as memory 406 or persistent storage 408.

Program code 418 is located in a functional form on computer-readable media 420 that is selectively removable and may be loaded onto or transferred to data processing system 400 for execution by processor unit 404. Program code 418 and computer-readable media 420 form computer program product 422 in these examples. In one example, computer-readable media 420 may be computer-readable storage media 424 or computer-readable signal media 426.

Computer-readable storage media 424 may include, for example, an optical or magnetic disk that is inserted or placed into a drive or other device that is part of persistent storage 408 for transfer onto a storage device, such as a hard drive, that is part of persistent storage 408. Computer-readable storage media 424 also may take the form of a persistent storage, such as a hard drive, a thumb drive, or a flash memory, that is connected to data processing system 400. In some instances, computer-readable storage media 424 may not be removable from data processing system 400.

In these examples, computer-readable storage media 424 is a physical or tangible storage device used to store program code 418 rather than a medium that propagates or transmits program code 418. Computer-readable storage media 424 is also referred to as a computer-readable tangible storage device or a computer-readable physical storage device. In other words, computer-readable storage media 424 is a media that can be touched by a person.

Alternatively, program code 418 may be transferred to data processing system 400 using computer-readable signal media 426. Computer-readable signal media 426 may be, for example, a propagated data signal containing program code 418. For example, computer-readable signal media 426 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 418 may be downloaded over a network to persistent storage 408 from another device or data processing system through computer-readable signal media 426 for use within data processing system 400. For instance, program code stored in a computer-readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different illustrative embodiments may be implemented in a data processing system including components in addition to and/or in place of those illustrated for data processing system 400. Other components shown in FIG. 5 can be varied from the illustrative examples shown. The different embodiments may be implemented using any hardware device or system capable of running program code. As one example, data processing system 400 may include organic components integrated with inorganic components and/or may be comprised entirely of organic components excluding a human being. For example, a storage device may be comprised of an organic semiconductor.

In another illustrative example, processor unit 404 may take the form of a hardware unit that has circuits that are manufactured or configured for a particular use. This type of hardware may perform operations without needing program code to be loaded into a memory from a storage device to be configured to perform the operations.

For example, when processor unit 404 takes the form of a hardware unit, processor unit 404 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a field programmable logic array, a field programmable gate array, and other suitable hardware devices. With this type of implementation, program code 418 may be omitted, because the processes for the different embodiments are implemented in a hardware unit.

In still another illustrative example, processor unit 404 may be implemented using a combination of processors found in computers and hardware units. Processor unit 404 may have a number of hardware units and a number of processors that are configured to run program code 418. With this depicted example, some of the processes may be implemented in the number of hardware units, while other processes may be implemented in the number of processors.

In another example, a bus system may be used to implement communications framework 402 and may be comprised of one or more buses, such as a system bus or an input/output bus. Of course, the bus system may be implemented using any suitable type of architecture that provides for a transfer of data between different components or devices attached to the bus system.

Additionally, communications unit 410 may include a number of devices that transmit data, receive data, or both transmit and receive data. Communications unit 410 may be, for example, a modem or a network adapter, two network adapters, or some combination thereof. Further, a memory may be, for example, memory 406, or a cache, such as that found in an interface and memory controller hub that may be present in communications framework 402.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Illustrative Distributed Data Processing System

Figure 6:
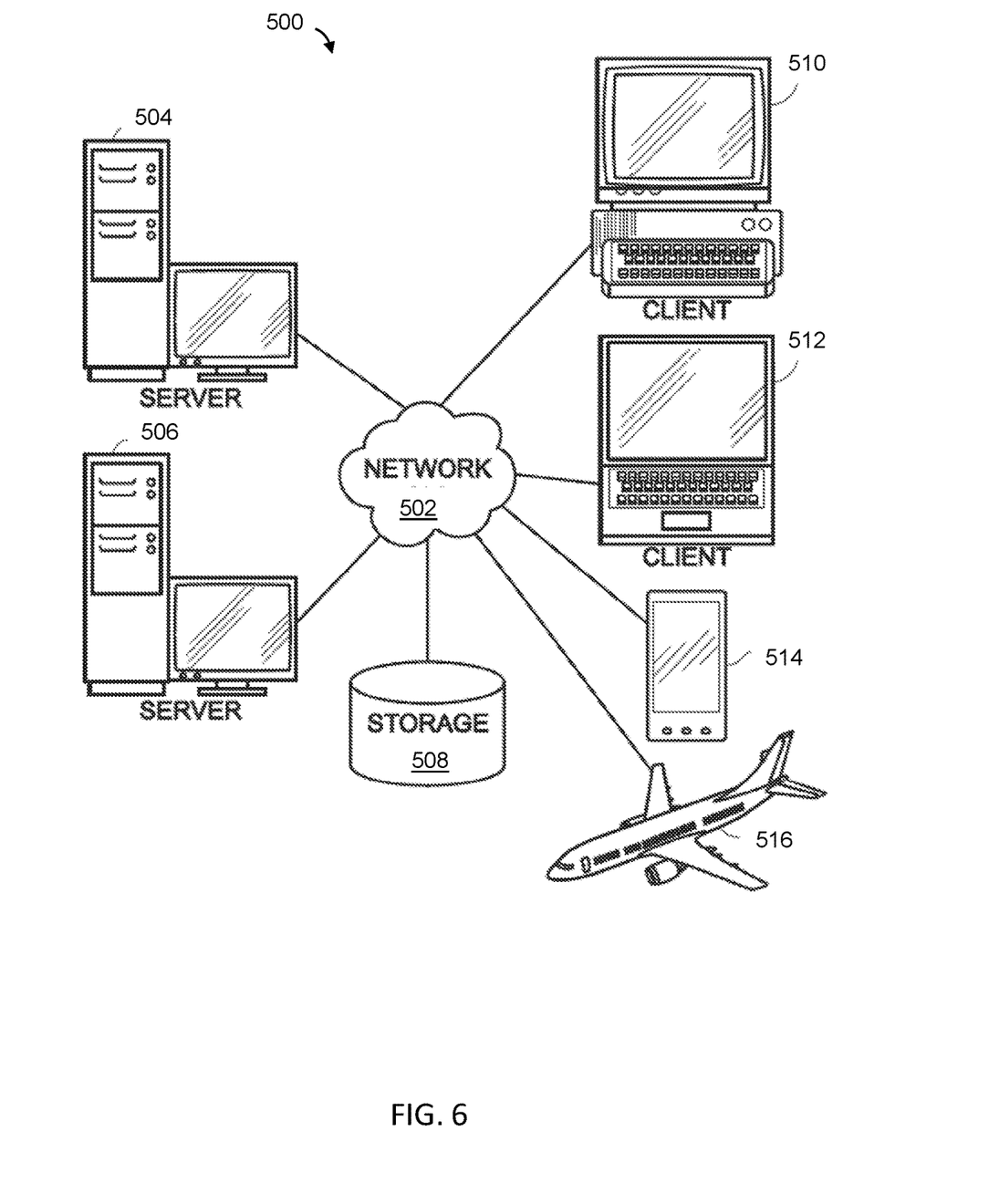
FIG. 6 is an illustrative distributed data processing system suitable for use with and/or inclusion in one or more aspects of the present disclosure.

As shown in FIG. 6, this example describes a general network data processing system 500, interchangeably termed a network, a computer network, a network system, a distributed data processing system, or a distributed network, aspects of which may be included in one or more illustrative embodiments of structural health monitoring systems and methods. For example, the structural health monitoring devices may communicate with the reader or readers over a computer network. The monitoring devices may be nodes or clients of a network. Aspects of a computer network may also be used to analyze or collate the measurement data from one or more monitoring devices. In some examples, a reader computer onboard a host aircraft may communicate with other computers via a network.

It should be appreciated that FIG. 6 is provided as an illustration of one implementation and is not intended to imply any limitation with regard to environments in which different embodiments may be implemented. Many modifications to the depicted environment may be made.

Network data processing system 500 is a network of computers, each of which is an example of data processing system 400, and other components. Network data processing system 500 may include network 502, which is a medium configured to provide communications links between various devices and computers connected together within network data processing system 500. Network 502 may include connections such as wired or wireless communication links, fiber optic cables, and/or any other suitable medium for transmitting and/or communicating data between network devices, or any combination thereof.

In the depicted example, a first network device 504 and a second network device 506 connect to network 502, as does an electronic storage device 508. Network devices 504 and 506 are each examples of data processing system 400, described above. In the depicted example, devices 504 and 506 are shown as server computers. However, network devices may include, without limitation, one or more personal computers, mobile computing devices such as personal digital assistants (PDAs), tablets, and smart phones, handheld gaming devices, wearable devices, tablet computers, routers, switches, voice gates, servers, electronic storage devices, imaging devices, and/or other networked-enabled tools that may perform a mechanical or other function. These network devices may be interconnected through wired, wireless, optical, and other appropriate communication links.

In addition, client electronic devices, such as a client computer 510, a client laptop or tablet 512, and/or a client smart device 514, may connect to network 502. Each of these devices is an example of data processing system 400, described above regarding FIG. 5. In some examples, communications-enabled data processing systems on one or more aircraft 516 may connect to network 502. Client electronic devices 510, 512, 514, and 516 may include, for example, one or more personal computers, network computers, and/or mobile computing devices such as personal digital assistants (PDAs), smart phones, handheld gaming devices, wearable devices, and/or tablet computers, and the like. In the depicted example, server 504 provides information, such as boot files, operating system images, and applications to one or more of client electronic devices 510, 512, 514, and 516. Client electronic devices 510, 512, 514, and 516 may be referred to as "clients" with respect to a server such as server computer 504. Network data processing system 500 may include more or fewer servers and clients or no servers or clients, as well as other devices not shown.

Client smart device 514 may include any suitable portable electronic device capable of wireless communications and execution of software, such as a smartphone or a tablet. Generally speaking, the term "smartphone" may describe any suitable portable electronic device having more advanced computing ability and network connectivity than a typical mobile phone. In addition to making phone calls (e.g., over a cellular network), smartphones may be capable of sending and receiving emails, texts, and multimedia messages, accessing the Internet, and/or functioning as a web browser. Smart devices (e.g., smartphones) may also include features of other known electronic devices, such as a media player, personal digital assistant, digital camera, video camera, and/or global positioning system. Smart devices (e.g., smartphones) may be capable of connecting with other smart devices, computers, or electronic devices wirelessly, such as through near field communications (NFC), BLUETOOTH, WiFi, or mobile broadband networks. Wireless connectively may be established among smart devices, smartphones, computers, and other devices to form a mobile network where information can be exchanged.

Program code located in system 500 may be stored in or on a computer recordable storage medium, such as persistent storage 408 described above, and may be downloaded to a data processing system or other device for use. For example, program code may be stored on a computer recordable storage medium on server computer 504 and downloaded for use to client 510 over network 502 for use on client 510.

Network data processing system 500 may be implemented as one or more of a number of different types of networks. For example, system 500 may include an intranet, a local area network (LAN), a wide area network (WAN), or a personal area network (PAN). In some examples, network data processing system 500 includes the Internet, with network 502 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 500 may be referred to as a "cloud." In those examples, each server 504 may be referred to as a cloud computing node, and client electronic devices may be referred to as cloud consumers, or the like. FIG. 6 is intended as an example, and not as an architectural limitation for any illustrative embodiments.

Additional Examples and Illustrative Combinations

This section describes additional aspects and features of structural health monitoring systems and methods, presented without limitation as a series of paragraphs, some or all of which may be alphanumerically designated for clarity and efficiency. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

A0. A structural health monitoring device comprising:
a measuring circuit including a processing circuit communicatively coupled to a pair of electrodes attachable to a target area of a workpiece, the measuring circuit in communication with a radio circuit having an antenna configured to facilitate offboard communication; and
an energy harvester circuit configured to provide electrical power to the measuring circuit;
wherein the measuring circuit is configured to measure an impedance of the target area of the workpiece; and
wherein the processing circuit is configured to determine a change in the impedance of the target area indicative of a change in structural health of the workpiece.

A1. The device of paragraph A0, wherein the energy harvester circuit comprises an energy harvesting integrated circuit coupled to a thermoelectric generator.

A2. The device of any of paragraphs A0 through A1, wherein the energy harvester circuit comprises an energy storage device.

A3. The device of paragraph A2, wherein the energy storage device comprises a rechargeable lithium-ion battery.

A4. The device of any of paragraphs A0 through A3, wherein the measuring circuit is communicatively coupled to an onboard memory store.

A5. The device of any of paragraphs A0 through A4, wherein the measuring circuit is configured to measure at least two different electrical characteristics of the target area of the workpiece.

B0. A structural health monitoring system comprising:
a structural health monitoring device comprising a measuring circuit including a processing circuit communicatively coupled to a pair of electrodes attachable to a target area of a workpiece, the measuring circuit in communication with a radio circuit having an antenna configured to facilitate offboard communication; and
an energy harvester circuit configured to provide electrical power to the measuring circuit;
wherein the measuring circuit is configured to measure an impedance of the target area of the workpiece; and
wherein the processing circuit is configured to determine a change in the impedance of the target area indicative of a change in structural health of the workpiece; and
a reader configured to wirelessly interrogate the structural health monitoring device to obtain information regarding the change in the impedance of the target area.

B1. The device of paragraph B0, wherein the energy harvester circuit comprises an energy harvesting integrated circuit coupled to a thermoelectric generator.

B2. The device of any of paragraphs B0 through B1, wherein the energy harvester circuit comprises an energy storage device.

B3. The device of any of paragraphs B0 through B2, wherein the workpiece comprises a portion of an aircraft, and the reader comprises an onboard network system of the aircraft.

B4. The device of any of paragraphs B0 through B3, wherein the reader comprises a portable RFID reader configured to communicate with the antenna and the radio circuit of the structural health monitoring device.

B5. The device of any of paragraphs B0 through B4, wherein the measuring circuit is communicatively coupled to an onboard memory store.

C0. A method for structural health monitoring, the method comprising:
    monitoring structural health of a workpiece using a structural health monitoring device coupled to the workpiece, the structural health monitoring device comprising a measuring circuit including a processing circuit communicatively coupled to a pair of electrodes attached to a target area of the workpiece, wherein the measuring circuit is configured to measure an impedance of the target area of the workpiece, and wherein the processing circuit is configured to determine a change in the measured impedance of the target area indicative of a change in structural health of the workpiece;
    harvesting environmental energy using an energy harvesting circuit of the structural health monitoring device to provide electrical power to the structural health monitoring device; and
    transmitting information regarding the measured impedance of the target area to an offboard reader using a radio circuit of the structural health monitoring device in communication with the measuring circuit.

C1. The method of paragraph C0, further comprising comparing the measured impedance of the target area of the workpiece to an expected impedance range.

C2. The method of paragraph C1, further comprising, in response to the measured impedance being outside the expected impedance range, sending an alert signal to the offboard reader.

C3. The method of any of paragraphs C0 through C2, further comprising storing the measured impedance in a memory store of the measuring circuit.

C4. The method of any of paragraphs C0 through C3, wherein harvesting environmental energy comprises harvesting thermal energy using a thermoelectric generator (TEG) coupled to an energy harvester integrated circuit (IC).

C5. The method of any of paragraphs C0 through C4, wherein harvesting environmental energy comprises harvesting solar energy using a photovoltaic cell coupled to an energy harvester IC.

C6. The method of any of paragraphs C0 through C5, wherein the workpiece comprises a portion of an aircraft, and the offboard reader comprises an onboard network system (ONS) of the aircraft.

C7. The method of any of paragraphs C0 through C6, wherein the energy harvesting circuit comprises an electrical power storage device.

C8. The method of any of paragraphs C0 through C7, wherein harvesting environmental energy includes harvesting energy from an electromagnetic interrogation signal received from the offboard reader.

C9. The method of any of paragraphs C0 through C8, further comprising aggregating the transmitted information regarding the measured impedance and conducting a trend analysis on the aggregated information.

Conclusion

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A structural health monitoring device comprising:
    a measuring circuit including a processing circuit communicatively coupled to a pair of electrodes attachable to a target area of a workpiece, the measuring circuit in communication with a radio circuit having an antenna configured to facilitate offboard communication; and
    an energy harvester circuit configured to provide electrical power to the measuring circuit;
    wherein the measuring circuit is configured to measure an impedance of the target area of the workpiece;
    wherein the processing circuit is configured to determine a change in the impedance of the target area indicative of a change in structural health of the workpiece; and
    wherein the radio circuit is configured to transmit information received from the measuring circuit regarding a measured impedance of the target area to an offboard reader.

2. The device of claim 1, wherein the energy harvester circuit comprises an energy harvesting integrated circuit coupled to a thermoelectric generator.

3. The device of claim 1, wherein the energy harvester circuit comprises an energy storage device.

4. The device of claim 3, wherein the energy storage device comprises a rechargeable lithium-ion battery.

5. The device of claim 1, wherein the measuring circuit is communicatively coupled to an onboard memory store.

6. The device of claim 1, wherein the measuring circuit is configured to measure at least two different electrical characteristics of the target area of the workpiece.

7. A structural health monitoring system comprising:
    a structural health monitoring device comprising a measuring circuit including a processing circuit communicatively coupled to a pair of electrodes attachable to a target area of a workpiece, the measuring circuit in communication with a radio circuit having an antenna configured to facilitate offboard communication; and
    an energy harvester circuit configured to provide electrical power to the measuring circuit;
    wherein the measuring circuit is configured to measure an impedance of the target area of the workpiece; and
    wherein the processing circuit is configured to determine a change in the impedance of the target area indicative of a change in structural health of the workpiece; and
    a reader configured to receive information regarding a measured impedance of the target area transmitted from the antenna and wirelessly interrogate the structural health monitoring device to obtain information regarding the change in the impedance of the target area.

8. The device of claim 7, wherein the energy harvester circuit comprises an energy harvesting integrated circuit coupled to a thermoelectric generator.

9. The device of claim 7, wherein the energy harvester circuit comprises an energy storage device.

10. The device of claim 7, wherein the workpiece comprises a portion of an aircraft, and the reader comprises an onboard network system of the aircraft.

11. The device of claim 7, wherein the reader comprises a portable radio-frequency identification (RFID) reader configured to communicate with the antenna and the radio circuit of the structural health monitoring device.

12. The device of claim 7, wherein the measuring circuit is communicatively coupled to an onboard memory store.

13. A method for structural health monitoring, the method comprising:
monitoring structural health of a workpiece using a structural health monitoring device coupled to the workpiece, the structural health monitoring device comprising a measuring circuit including a processing circuit communicatively coupled to a pair of electrodes attached to a target area of the workpiece, wherein the measuring circuit is configured to measure an impedance of the target area of the workpiece, and wherein the processing circuit is configured to determine a change in the measured impedance of the target area indicative of a change in structural health of the workpiece;
harvesting environmental energy using an energy harvesting circuit of the structural health monitoring device to provide electrical power to the structural health monitoring device; and
transmitting information regarding the measured impedance of the target area to an offboard reader using a radio circuit of the structural health monitoring device in communication with the measuring circuit.

14. The method of claim 13, further comprising comparing the measured impedance of the target area of the workpiece to an expected impedance range.

15. The method of claim 14, further comprising, in response to the measured impedance being outside the expected impedance range, sending an alert signal to the offboard reader.

16. The method of claim 13, further comprising storing the measured impedance in a memory store of the measuring circuit.

17. The method of claim 13, wherein harvesting environmental energy comprises harvesting thermal energy using a thermoelectric generator (TEG) coupled to an energy harvester integrated circuit (IC).

18. The method of claim 13, wherein harvesting environmental energy comprises harvesting solar energy using a photovoltaic cell coupled to an energy harvester IC.

19. The method of claim 13, wherein the workpiece comprises a portion of an aircraft, and the offboard reader comprises an onboard network system (ONS) of the aircraft.

20. The method of claim 13, wherein the energy harvesting circuit comprises an electrical power storage device.

* * * * *